United States Patent [19]

Ogasa et al.

[11] 4,039,386

[45] Aug. 2, 1977

[54] METHOD FOR DETERMINING THE VIABLE BACTERIA COUNT OF FOOD AND A MEDIUM FOR ACCOMPLISHING THE METHOD

[75] Inventors: Katsuhiro Ogasa; Seiichi Shimamura, both of Yokohama; Hiroshi Miyagawa, Kamakura, all of Japan

[73] Assignee: Morinaga Milk Industry Co., Ltd., Tokyo, Japan

[21] Appl. No.: 673,294

[22] Filed: Apr. 2, 1976

[51] Int. Cl.² .............................................. C12K 1/10
[52] U.S. Cl. .............................. 195/100; 195/103.5 R
[58] Field of Search ................. 195/99, 100, 101, 102, 195/103, 103.5 R

[56] References Cited

U.S. PATENT DOCUMENTS 3,107,204  10/1963  Brown et al. ................. 195/103.5 K
3,902,969  9/1975   Gold ............................. 195/103.5 R

*Primary Examiner*—Lionel M. Shapiro
*Assistant Examiner*—Robert J. Warden
*Attorney, Agent, or Firm*—Oblon, Fisher, Spivak, McClelland & Maier

[57] ABSTRACT

A method of determining the viable bacterial count of food which comprises incubating said food in a liquified agar medium which contains from 0.005 to 0.1 gram per liter of said liquified agar medium 2, 3, 5-triphenyl tetrazolium chloride as an inhibitor of bacteria colony spreading, and counting the bacteria colonies.

2 Claims, 2 Drawing Figures

METHOD FOR DETERMINING THE VIABLE BACTERIA COUNT OF FOOD AND A MEDIUM FOR ACCOMPLISHING THE METHOD

BACKGROUND OF THE INVENTION

1. Field of the Invention

The present invention relates to a method of determining the total viable bacteria count of Enterobacteriaceae which is capable to or forming spreading colonies or spreaders and of causing food poisoning, sporeforming bacteria which are difficult to destroy using ordinary heat treatment during food processing, and other bacteria in food at the same time, and to a powdery medium for determining the viable bacterial counts of food, whereby the bacteria count can be determined without the formation of a spreading colony.

2. Description of the Prior Art

From the present technical level of microbiology, it would appear to be a simple matter to determine the viable bacteria count of food.

However, when an agar medium, which is conventionally used in practice, is used for determining the viable bacteria count by forming colonies on a plate of said agar medium and counting the numbers of viable bacterium, it is often experienced that certain kinds of bacterium present undergo an extraordinary spreading of their colonies. Typically, the neighbouring colonies contact each other and, in the extreme case, the colonies spread over all the surface of the medium plate which makes the exact count of number of colonies present impossible.

The "Spreading of Colonies" or the formation of "Spreaders" can be avoided to some degree by completely drying the surface of medium plate so that no water drops are remain at the time of incubation. But in some bacteria it is difficult to prevent "Spreading of Colonies" of these bacteria even if the drying is complete, and only a few colonies spread all over the surface of medium plate. When the number of colonies becomes greater than 100 per each plate, spreading can hardly be prevented.

Bacteria liable to form spreading colonies include Proteus, Escherichia, Aerobacter, Serratia and the like which belong to Enterobacteriaceae (Bacteriological Reviews, 36, 478, 1972 and Bergey's Manual of Determinative Bacteriology, page 322, 7th Edition, The Wiliam & Wilkins Company, Baltimore, U.S.A., 1957). All of these bacteria participate in spoilage of food and in the outbreak of food poisoning.

However, bacteria which form spreading colonies most remarkably are sporeformers. The sporeformers have two kinds of genus, that is, aerobic Bacillus and anaerobic Clostridium. These bacteria have the characteristic of easily forming spreading colonies and include a pathogenic species such as Bacillus anthracis and Clostridium botulinum and many other bacteria which survive through the heating and pasteurizing step of food processing and cause the deterioration food in distribution.

The bacteria capable of forming spreading colonies, as described above, are widely distributed in nature and have a wide temperature range of growth, and, therefore, from a viewpoint of food hygiene, it is an important problem to determine the viable count of these bacteria in food exactly. However, the conventional method for the determination or the viable bacteria count does not take any steps to prevent the formation of spreading colonies at the time of incubation of bacteria. Therefore, on page 48 of "Standard Methods for the Examination of Dairy Products" 12th edition published by the American Public Health Association, Inc. New York, (1967), it is stipulated that if spreaders occur on the plate(s) selected, one counts the colonies on representative portions thereof only when (1) colonies are well distributed in spreader-free areas and (2) the area covered by spreader(s), including total repressed-growth area, if any, does not exceed one-half of plate. However, in case of using the conventional medium, errors are in any case unavoidable and it is too much to say that the counts in a case where a spreading colony is actually formed is only an estimated value.

As a result of studying the difficulty of determining viable counts of food-contaminating bacteria which form spreading colonies, the present inventors have found that 2, 3, 5-triphenyl-tetrazolium chloride (hereinafter abbreviated to TTC) can prevent the spreading of the bacteria and the formation of spreading colonies without inhibiting the growth of bacterium not forming a spreading colony. The inventors have further found that an incubation plate which contains no spreading colonies is obtained by using said compound, TTC, as the component of a medium conventionally used for the determination of viable bacterial counts of food so that a more exact determination of viable bacterial counts becomes possible.

An aqueous solution of TTC is colorless but it turns red by the reduction reaction due to the convertion of TTC to insoluble formozan. TTC has hitherto been used as an indicator for testing the growth of bacteria by utilizing this characteristic. For example, TTC has been used for testing antibiotics in cow's milk. (Neal et al, Journal of Dairy Science, 38, 629, 1955) and judging for the quality of pasteurized milk (Broitman et al, Journal of Milk and Food Technology, 19, 63, 1956). In these reports TTC is employed as an indicator utilizing the phenomenon that TTC is reduced by the growth of bacteria in cow's milk medium and colored.

On the other hand to CVT medium reported by Olsen, which is a selective medium for psychrophilic bacterium, (Journal of Dairy Science, 46, 362, 1963) and EF medium placed on the market by Nissui Pharmaceutical Co., Ltd., which is a medium for the identification of Enterococcus, is added 0.005% and 0.015%, respectively, of TTC. Either of these media are used for classification of bacteria according to the depth of color tone of growth colony caused by the difference of the reducing activity of various bacteria for TTC.

Also, the Japanese Patent Public Disclosure Gazette No. 125081/75 describes a method of easily detecting coliform bacilli group in a sample by directly contacting a filter paper strip impregnated with an aqueous solution of TTC and liquefied agar medium to the sample. However, in this method TTC is used as a selective agent for inhibiting the growth of fungus and gram-positive bacteria, and for the purpose of determining total viable bacterial counts of the sample, the filter paper strip impregnated with TTC and medium cannot be utilized.

As described above, TTC has hitherto been employed for identification of specific substance or isolation and classification of specific bacterium in a specific medium, but has not been used for preventing the formation of spreading colonies, as a component of medium for determining the viable bacterial count of food.

SUMMARY OF THE INVENTION

An object of the present invention is to provide an improved method of determining the viable bacterial count of food, which is very advantageous for food hygiene. The method comprises preventing the formation of spreading colonies which are peculiarly found in sporeforming bacteria and a certain kind of bacterium belonging to Enterobacteriaceae. This makes the determination of the viable bacterial count of food more exact and easier in the case of counting the colonies by the plate incubating method, and a medium used for the same method.

The object has been accomplished by a method of determining the viable bacteria count of which is contaminated with spreading-colony forming bacteria, which is characterized by using a liquefied agar medium having the conventional composition for determining the viable bacterial count of food containing 2, 3, 5-triphenyl tetrazolium chloride as an inhibitor of colony spreading in an amount of 0.005 to 0.1g per 1l of said liquefied agar medium, and a powdery agar medium for determining the viable bacterial count of food which is contaminated with spreading-colony forming bacteria, which has the conventional composition for determining viable bacterial counts of food and is characterized by containing 2, 3, 5-triphenyl tetrazolium chloride as an inhibitor of colony spreading in an amount of 0.005 to 0.1g per 1l of said liquefied agar medium when dissolved in water, according to the present invention.

DETAILED DESCRIPTION OF THE PREFERRED EMBODIMENT

Figure 1:
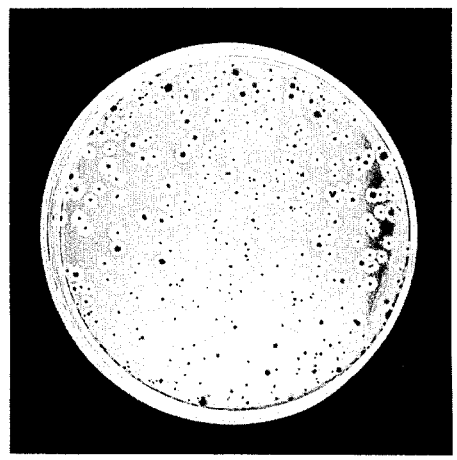
FIG. 1 and FIG. 2 show a photograph of colony of Bacillus lichemiformis IAM 11054 incubated using the Standard Agar Medium with TTC (the present invention) and without TTC, respectively.

The powdery medium described as an agar medium for determining the viable bacterial count of food in the present invention is not so called "selective medium" for the purpose of selectively isolating only a specific kind of bacterium from numerous kinds of bacterium by adding a bacterium growth inhibitor such as bile acid salts, antibiotics, and the like, but a medium in which various kinds of bacterium in food can be grown and which has been widely used for determining the viable bacterial counts of food. As example of these media, Standard Agar Medium (made by Eiken Chemical Co., Ltd., Nissui Pharmaceutical Co., Ltd., Kyokuto Pharmaceutical Industry Co., Ltd. -- hereinafter abbreviated to Eiken, Nissui and Kyokuto, respectively), Nutrient Agar Medium (made by Eiken, Nissui, Kyokuto), Tryptosoy Agar Medium (made by Eiken), Tryptosoya Agar Medium (made by Nissui, Kyokuto), Standard Methods Agar Medium (made by Baltimore Biological Laboratory Co., Difco Laboratory Incorporated -- hereinafter abbreviated to B.B.L. Difco, respectively), Nutrient Agar Medium (made by B.B.L., Difco, Oxoid Limited), Tryptic Soy Agar Medium (made by Difco), Trypticase Soy Agar Medium (made by B.B.L.) and Tryptone Soya Agar Medium (made by Oxoid Limited -- hereinafter abbreviated to Oxoid) used for aerobic bacterium, and Anaerobe Agar Medium (made by Eiken), GAM Agar Medium (made by Nissui) and the like used for anaerobic bacterium are on the market in a form of powder.

The powdery medium of the present invention is prepared by adding TTC to an agar medium for determining viable bacterial counts of food at the rate of 0.005 to 0.1g of TTC per 1l of the medium dissolved in water and mixing them uniformly. TTC which is one component of the medium of the present invention is added for the purpose of preventing the formation of spreading colonies, and the amount of TTC added is 0.005 to 0.1g, desirably 0.02 to 0.08g, per 1l of the liquefied medium from the result of test as described below. The present medium contains, besides TTC, peptone and tryptone as a nitrogen source, glucose as a carbon source and sodium, phosphorous and others as an ash component necessary for the growth of bacterium and additionally an agar as a shaping agent for forming the plate. These components are used at the various rates similarly as in the commercially available media as described above.

The process for preparing the present medium and one example of the composition of the medium are as follows:

50g of powdery yeast extract (made by Kyokuto), 100g of powdery peptone (made by Kyokuto), 20g of glucose (Guaranteed reagent made by Wako Junyaku Industry Co., Ltd.), 0.8g of TTC (Guaranteed reagent made by Wako Junyaku Industry Co., Ltd.) and 300g of Bacto-agar powder (made by Difco) were fully mixed by a V type of mixer to obtain about 470g of the powdery medium of the present invention. On the occasion of use 23.5g of the medium are dissolved in 1l of water. The composition of the liquefied medium is 2.5g of yeast extract, 5g of peptone, 1g of glucose, 0.04g of TTC and 15g of agar per 1l.

The method of the present invention will be further explained more in detail.

The method of the present invention comprises dissolving the medium of the present invention as described before in a prescribed amount of water, heating and sterilizing it according to the conventional method, making a plate therefrom, smearing a food sample thereon, or pour plating a food sample with the medium, incubating it aerobically or anaerobically at at a stated temperature for a stated time and thereafter counting a number of colony formed. Under the conditions of heating and sterilizing a medium, TTC is sometimes decomposed thermally and the medium turns pink slightly, however, it does not interfere with the determination of viable bacterial counts of food.

The present method is the same as the conventional method, for example, as the method described on pages 103 to 106 of "Guide to Inspection in Food Hygiene (I)" prepared under the supervision of the Ministry of Public Welfare in incubation condition such as incubation time, incubation temperature, and the like and in procedure of determining viable bacterial counts of food. And also, in case of using the above described agar medium on the market for determining viable bacterial counts of food in the present method, the medium is dissolved in water and TTC is added thereto at the rate of 0.005 to 0.1g of TTC per 1l of the medium and dissolved.

The following tests were carried out for determining the amount of TTC added as a medium component:

Test 1 Test with aerobic bacterium

In this test ten kinds of medium prepared by the same method as described above with the exception of adjusting the amount of TTC (Guaranteed reagent made by Wako Junyaku Industry Co., Ltd.) to a rate of 0.0025 to 0.14g of TTC per 1l of medium dissolved in water and the Standard Agar Medium (Eiken) not containing TTC as a control, i.e. eleven kinds in total, were used as shown in Table 1. Each 23.5g of each medium added with TTC and Standard Agar Medium were dissolved in 1l of water and sterilized.

As described in Table 1, five strains of Bacillus and Escherichia coli 0-111, i.e. six kinds in total, were provided to the test. Each platinum loop of colony of Bacillus and Escherichia coli 0-111 was taken from slant medium of stock culture, inoculated into 15ml of Tryptosoy Bouillon Medium (Eiken) and incubated at 37° C for 20 hours to obtain cell suspensions for test. 1.0ml of the cell suspension was mixed with each 20ml of the above described eleven kinds of sterilized medium and incubated by the conventional pour plate method. The time and temperature of incubation were 37° C and 48 hours, respectively.

The counting of colonies was made on the plates in various dilution ratio of cell suspension and the object of counting was the plates in the dillution ratio wherein grown colonies is occured in the range of 30 to 300. Therefore, in the incubation held in eleven kinds of medium for one test strain, when in one medium a number of colony was 30 to 300 in a dilution ratio, while in a certain medium a spreading colony was formed in the same dilution ratio and even if a number of colony counted in the plate of ten times higher or lower dilution ratio is less than 30 or more than 300 per one plate, these values were not recorded. A number of colony is a value of counted number of colony on a plate multiplied by a dilution multiple of sample. The degree of the formation of spreading colony was shown by +++ for the degree that the colony spreads over almost the whole surface of medium plate, ++ for the degree that the colony spreads over above about ½ of the area of a plate, + for the degree that the colony spreads over below about ½ of the area of a plate, and − for the degree that the spreading colony is scarcely or not observed. And the counting of colony was conducted only for a plate in which the degree of spreading colony is + or −, and the number of colony on a plate in the degree of +++ or ++ was recorded L.A. for short as a laboratory accident, according to the description of "Standard Methods for the Examination of Dairy Products". The test results are as shown in Table 1.

Table 1

| Test strain | | 0 (Control) | 0.0025 | 0.005 | 0.01 | 0.02 | 0.04 | 0.06 | 0.08 | 0.10 | 0.12 | 0.14 |
|---|---|---|---|---|---|---|---|---|---|---|---|---|
| Escherichia coli 0-111 | Number of colony | $43 \times 10^6$ | $49 \times 10^6$ | $47 \times 10^6$ | $51 \times 10^6$ | $54 \times 10^6$ | $58 \times 10^6$ | $55 \times 10^6$ | $62 \times 10^6$ | $56 \times 10^6$ | $58 \times 10^6$ | $50 \times 10^6$ |
| | Degree of spreading colony | + | + | + | − | − | − | − | − | − | − | − |
| Bacillus subtilis ATCC 6633 | Number of colony | L.A. | L.A. | $33 \times 10^6$ | $36 \times 10^6$ | $38 \times 10^6$ | $34 \times 10^6$ | $37 \times 10^6$ | $33 \times 10^6$ | $34 \times 10^6$ | $287 \times 10^5$ | $270 \times 10^5$ |
| | Degree of spreading colony | +++ | ++ | − | − | − | − | − | − | − | − | − |
| Bacillus licheniformis IAM 11054 | Number of colony | L.A. | L.A. | $145 \times 10^6$ | $150 \times 10^6$ | $143 \times 10^6$ | $148 \times 10^6$ | $148 \times 10^6$ | $151 \times 10^6$ | $143 \times 10^6$ | $139 \times 10^6$ | $128 \times 10^6$ |
| | Degree of spreading colony | +++ | ++ | − | − | − | − | − | − | − | − | − |
| Bacillus coagulans NIAH OSG-4 | Number of colony | L.A. | $99 \times 10^6$ | $100 \times 10^6$ | $96 \times 10^6$ | $96 \times 10^6$ | $103 \times 10^6$ | $100 \times 10^6$ | $97 \times 10^6$ | $105 \times 10^6$ | $94 \times 10^6$ | $88 \times 10^6$ |
| | Degree of spreading colony | ++ | − | − | − | − | − | − | − | − | − | − |
| Bacillus cereus IAM 1072 | Number of colony | L.A. | $205 \times 10^5$ | $223 \times 10^5$ | $219 \times 10^5$ | $230 \times 10^5$ | $218 \times 10^5$ | $211 \times 10^5$ | $214 \times 10^5$ | $222 \times 10^5$ | $200 \times 10^5$ | $177 \times 10^5$ |
| | Degree of spreading colony | +++ | + | − | − | − | − | − | − | − | − | − |
| Bacillus polymyxa NIAH 474 | Number of colony | L.A. | $31 \times 10^6$ | $44 \times 10^6$ | $46 \times 10^6$ | $50 \times 10^6$ | $54 \times 10^6$ | $57 \times 10^6$ | $53 \times 10^6$ | $36 \times 10^6$ | $235 \times 10^5$ | $169 \times 10^5$ |
| | Degree of spreading, colony | +++ | + | + | − | − | − | − | − | − | − | − |

(Note)
1) Number of colonies is the number of colonies per 1ml of test cell suspension
2) ATCC: American Type Culture Collection, Rockvill, U.S.A.
3) IAM: Institute of Applied Microbiology, University of Tokyo, Japan.
4) NIAH: National Institute of Animal Health, Kodaira City, Tokyo, Japan.

(note) 1) Number of colonies is the number of colonies per 1ml of test cell suspension 2) ATCC: American Type Culture Collection, Rockvill, U.S.A.

3) IAM: Institute of Applied Microbiology, University of Tokyo, Japan.

4) NIAH: National Institute of Animal Health, Kodaira City, Tokyo, Japan.

Figure 2:
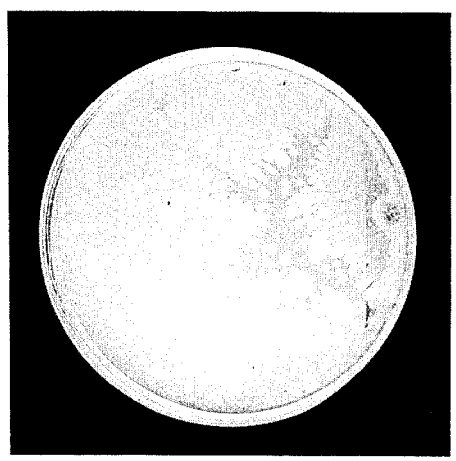

As is evident from Table 1, when using the control medium, a spreading colony was observed to occupy above about ½ of a plate area in test bacteria other than Escherichia coli 0-111, and, therefore, determination of viable bacterial counts was impossible. In contrast, in a medium added with above 0.005g of TTC per 1l of medium, such phenomenon was not recognized. And if the concentration of TTC is above 0.005g of per 1l of medium, a number of grown colony could be exactly counted and, in particular, when it is above 0.02g per 1l of medium, colonies uneven in size were not observed. Moreover all colonies turn red, and, in some kinds of bacterium, the central portion of red colony was rich in red color as if it is a core so that individual colonies could be very easily distinguished. This is evident from FIGS. 1 and 2. FIG. 1 is a photograph showing the state of colony when incubating Bacillus licheniformis IAM 11054 on the medium of the present invention prepared by adding TTC to the same medium as in Test 1 at the rate of 0.04g of TTC per 1l of medium. FIG. 2 is a photograph showing the state of colony when incubating the same strain on the control medium not added with TTC.

In the test results of Escherichia coli 0-111 on the control medium and B. cereus and B. polymyxa on a medium of 0.0025g/l in TTC concentration, spreading colony was recognized in the degree of less than ½ of a plate area, and the counted number of colony was lower than that in a medium higher in TTC concentration. This is owing to a fact that an apparent number of colony was decreased because spreading colonies formed in test bacterium for the deficiency of TTC concentration combined with adjacent colonies. When the TTC concentration was above 0.12g per 1l of medium, in some kinds of bacterium, the size of colony decreased and so the determined viable bacterial counts lowered. From this it seems that the high concentration of TTC in medium inhibits the growth of test bacterium. Therefore, the amount of TTC added for determining viable bacterial counts exactly is properly above 0.005g and below 0.10g per 1l of medium, in particular desirably 0.02 to 0.08 g/l. Within this range of the amount of TTC added, any inhibiting action of the medium on the growth of bacterium is not recognized. This is evident from the result of Test 3 as described after, in which a bacterium not forming a spreading colony was incubated on the medium of the present invention.

Test 2 Test with anaerobic bacterium

The medium and test cell suspension used in this test were prepared as follows:

Anaerobe agar medium (made by Eiken) on the market was dissolved in water by the conventional method, and TTC (Guaranteed reagent made by Wako Junyaku Industry Co., Ltd.) on the market was added thereto at the rate of 0.0025 to 0.14g of TTC per 1l of medium as shown in Table 2 and sterilized. Thus, ten kinds of medium containing TTC and one control medium, i.e. eleven kinds of plate medium in total, were prepared.

On the other hand, two strains of lyophilized Clostridium described in Table 2 were inoculated to 10ml of Thioglycolate medium (Eiken) and incubated at 37° C for 40 hours to prepare a test cell suspension. 0.1ml of the cell suspension was smeared onto the above described eleven kinds of plate medium by a Conradi rod and cultured anaerobically at 37° C for 72 hours by Steel wool method. Other procedures were the same as in Test 1. The results are as shown in Table 2.

determined viable bacterial counts are lowered. And in a medium added with above 0.12g of TTC per 1l of medium, an influence of growth inhibition was predicted and the same tendency as in aerobic bacterium was shown.

From the results of Tests 1 and 2, it was proved that, in case of determining viable bacterial counts of food using the medium of the present invention, viable counts of bacterium forming a spreading colony can be determined.

Next, the present inventors have tested whether or not the determining viable bacterial counts of food in case of using the medium of the present invention differs from that in case of using a conventional medium on the market.

Test 3 Test with a bacterium not forming a spreading colony

Staphylococcus aureus and Lactobacillus helveticus which do not form a spreading colony as shown in Table 3 were used as a test bacterium. Staphylococcus aureus and Lactobacillus helveticus were inoculated on Tryptosoy Bouillon Medium (Eiken) and skim milk medium prepared by reconstituting skim milk powder to 10% concentration, respectively, and incubated at 37° C for 20 hours to obtain test cell suspension. 1ml of the test cell suspension was plated with four kinds of medium differing in TTC concentration shown in Table 3 and incubated in the same manner as in Test 1 and a number of colony was counted. The results are as shown in Table 3.

Table 3

| | TTC concentration (g/l) | | | | |
|---|---|---|---|---|---|
| Test strain | 0 (Control) | 0.005 | 0.02 | 0.08 | 0.10 |
| Staphylococcus aureus RIMD 209p | $268 \times 10^6$ | $272 \times 10^6$ | $272 \times 10^6$ | $269 \times 10^6$ | $273 \times 10^6$ |
| Lactobacillus helveticus IAM-1042 | $57 \times 10^6$ | $56 \times 10^6$ | $60 \times 10^6$ | $58 \times 10^6$ | $57 \times 10^6$ |

(Note)
1) Number is the number of colonies per 1ml of test cell suspension
2) RIMD : Research Institute for Microbial Diseases, Osaka University, Osaka, Japan.

(Note) 1) Number is the number of colonies per 1ml of test cell suspension

Table 2

| Test strain | | 0 (Control) | TTC concentration (g/l) | | | | | | | | | |
|---|---|---|---|---|---|---|---|---|---|---|---|---|
| | | | 0.0025 | 0.005 | 0.01 | 0.02 | 0.04 | 0.06 | 0.08 | 0.10 | 0.12 | 0.14 |
| Clostridium butyricum ATCC 6014 | Number of colony | L.A. | $150 \times 10^4$ | $167 \times 10^4$ | $184 \times 10^4$ | $172 \times 10^4$ | $177 \times 10^4$ | $181 \times 10^4$ | $172 \times 10^4$ | $170 \times 10^4$ | $164 \times 10^4$ | $145 \times 10^4$ |
| | Degree of spreading colony | ++ | + | — | — | — | — | — | — | — | — | — |
| Clostridium sporogenes IAM 19234 | Number of colony | L.A. | $128 \times 10^4$ | $133 \times 10^4$ | $127 \times 10^4$ | $125 \times 10^4$ | $126 \times 10^4$ | $128 \times 10^4$ | $130 \times 10^4$ | $124 \times 10^4$ | $119 \times 10^4$ | $106 \times 10^4$ |
| | Degree of spreading colony | ++ | — | — | — | — | — | — | — | — | — | — |

(Note) Number of colonies is the number of colonies per 0.1m of test cell suspension As is evident from Table 2, even in case of incubating Clostridium, no formation of spreading colony was observed on a medium added with above 0.005g of TTC per 1l of medium in comparison with a medium without adding of TTC. However, in case of a certain kind of bacterium, spreading colonies were observed even on the medium added with 0.0025g of TTC per 1l of medium and combined each other and thereby the 2) RIMD : Research Institute for Microbial Diseases, Osaka University, Osaka, Japan.

As is evident from Table 3, the viable bacterial counts determined using the control medium not containing TTC is almost similar to the viable bacterial counts determined using the present medium added with TTC in various concentration and, therefore, in case of using the present medium, the growth inhibition of bacterium was never recognized.

The effect of the present invention is as follows:

1. The total viable bacterial counts including a bacterium forming a spreading colony can be exactly determined without inhibiting the growth of any bacterium:

2. Since the grown colony turns red, the colony can be very easily distinguished in case of pour plating with a sample which is dissolved in water to turn white, for example cow's milk, condensed milk, starch, and the like and such a sample as not dissolved in water and remaining fine pieces even if homogenized, for example a suspension of boiled rice, cheese, powdery spice and the like.

3. Since TTC is remarkably stable for heat, any special process for preparing the present medium is not needed.

4. The present medium is almost the same as the convention medium in cost since the amount of TTC used is very small.

5. In the test a special technique for preparing the medium is not needed.

6. Viable counts of bacterium forming a spreading colony in food can be determined in the same manner as in the conventionl method without requiring any special method.

EXAMPLE 1

200g of powdery yeast extract (Oxoid), 100g of "Lab-Lemco" beef extract (Oxoid), 500g of peptone L37 (Oxoid), 500g of Japanese Pharmacopoeia sodium chloride (made by Kanu Pharmaceutical Industry Co., Ltd), 1500g of agar powder (Oxoid) and 5g of TTC (Guaranteed reagent made by Wako Junyaku Pharmaceutical Industry Co., Ltd.) were sufficiently mixed by V-type mixer to obtain 2.8Kg of powdery medium. The powdery medium was dissolved in water at the rate of 28g of medium per $1l$ of water for use. The composition of the liquefied medium was 2g of yeast extract, 1g of "Lab-Lemco" beef extract, 5g of L37 peptone, 5g of Pharmacopoeia sodium chloride, 15g of agar and 0.05g of TTC per $1l$ of medium.

Using this medium and Nutrient Agar (Oxoid) on the market not containing TTC as a control, the following test was carried out:

10g of soy bean curd packaged in a container with the labeling of "pasteurized by high temperature process" were taken aseptically into a sterilized bottle and homogenized fully by a sterilized spattle to obtain a raw liquid in slurry state. The homogenized sample was stepwise diluted with sterilized physiologic saline by 10 times.

Each 1ml of the test suspension diluted to $10^5$ times was taken on four Petri dishes. The four Petri dishes in each dilution step were divided into two groups of two Petri dishes. About 20ml each of solution prepared by dissolving 56g of the medium of the present invention in $2l$ of water and sterilizing were poured into each dish of one of the groups and a solution prepared by dissolving 60g of nutrient agar in $2l$ of water and treated in the same manner as a control was poured into each dish of another group and either of them were incubated as 35° C for 48 hours.

The counting of colony was carried out on Petri dishes in which spreading colonies are scarcely or not observed and all colonies which can be enumerated with the naked eye were counted without limiting to the range of 30 to 300 each per one plate.

The degree of spreading colony formed was shown by $+ \sim +++$ in the same manner as in Test 1, and even if the degree is $+$, the number of colony was recorded if the counting is possible. The plate on which the number of colony is over 300 was counted using a calculation plate of densed colony. However, when the number of colony are so large that the measurement is impossible even by using said calculation plate, it was shown by $\infty$. The counted results of number of colony on each Petri dish are as shown in Table 4.

Table 4

| Kind of medium | Dilution ratio of sample | | | | | |
|---|---|---|---|---|---|---|
| | None | 10 | $10^2$ | $10^3$ | $10^4$ | $10^5$ |
| Medium of the present invention | $\infty$ | $\infty$ | 1435 | 152 | 16 | 3 |
| | $\infty$ | $\infty$ | 1466 | 158 | 10 | 4 |
| Control medium | +++ | +++ | +++ | ++ | ++ | 1 |
| | +++ | +++ | +++ | ++ | +, 9 | 3 |

(Note) number of colonies is the number of colonies per 1ml of test suspension (Note) Number of colonies is the number of colonies per 1ml of test suspension As is evident from Table 4, in the sample incubated on the medium of the present invention, the formation of spreading colony was not recognized and each of colony could be counted to a number of above 1,400 in $10^2$ of dilution ration, however, in the sample incubated in the conventional medium number of colony could not be counted even in $10^4$ of dilution ratio.

When determining the viable bacterial counts of sample according to the above description of "standard Methods for Examination of Diary Products", in case of using the medium of the present invention, since the number of colony in a specimen diluted by $10^3$ times is within the range of 30 to 300 each, the arithmetic mean value of two Petri dishes is 155, and so the viable bacterial counts were $16 \times 10^4/g$ rounding off the fractions to the third figure from high degree. In contrast, in case of using the control medium, although a value of below $30 \times 10^4/g$ was obtained at any rate according to the above "Standard Methods of Examination of Dairy Products", the exact viable bacterial counts could not be determined.

EXAMPLE 2

1.5Kg of Trypticase (B.B.L.), 0.5Kg of Phytone (B.B.L.), 0.5Kg of Japanese Pharmacopoeia sodium chloride (Kanu Pharmaceutical Industry Co., Ltd.), 1.5Kg of agaragar powder (Difco) and 5g of TTC (made by Eastman Kodak Co., Ltd.) were fully mixed by a V-type mixer to obtain 4Kg of powdery medium. The powdery medium was dissolved in water at the rate of 40g of medium per $1l$ of water for use. The composition of the liquefied medium was 15g of Trypticase, 5g of Phytone, 5g of sodium chloride, 15g of agar and 0.05 of TTC per $1l$ of the medium.

Using this medium and Trypticase Soy Agar Medium (B.B.L.) on the market not containing TTC as a control the following test was carried out:

10g of natural cheese were taken into a sterilized bottle and a small amount of sterilized physiological saline was added thereto and, after homogenized by a sterilized Spattle, was diluted by 10 times. Each 10ml of the 10 times diluted solution were taken into 2 sterilized test tubes. One of them was used for temperature measurement. These test tubes with diluted solution were immersed into a water bath to be heated at 80° C for 10 minutes exactly and immediately thereafter was immersed into a cold water to be cooled rapidly. Thus, a test suspension for determining a number of anaerobic sporeformers in natural cheese was prepared. The test suspension was diluted to $10^3$ times in the same manner as in Example 1 and each 0.1ml of diluted solution was smeared on the above described two medium plates using a Conradi rod. The smeared plates were placed into an anaerobic jar and incubated anaerobically at 37° C for 72 hours according to Steel wool method. The counting method of colony and judgement of degree of spreading colony were carried out in the same manner as in Example 1. The result for counting of number of colony are as shown in Table 5.

Table 5

| Kind of medium | Dilution ratio of sample | | |
|---|---|---|---|
| | 10 | $10^2$ | $10^3$ |
| Medium of the present invention | ∞ | 261 | 29 |
| | ∞ | 273 | 25 |
| Control Medium | +++ | +++ | +++ |
| | +++ | +++ | 16 |

(Note)
number of colonies is the number of colonies per 0.1ml of test suspension (Note) Number of colonies is the number of colonies per 0.1ml of test suspension As is evident from Table 5, in case of using the medium of the present invention, the number of anaerobic sporeformers in sample was determined at $27 \times 10^4$/g, in a medium not containing TTC, spreading colonies were remarkably formed and so viable bacterial counts could not be exactly determined although it was determined as below $30 \times 10^4$/g roughly according to the above described "Standard Methods of Examination of Dairy Products". Further, in case of using the present medium, in particular on a plate which is low in dilution ratio, fine cheese curd and colony is smeared test suspension can be distinctly distinguished with color tones, and, exact determination of viable bacterial counts is possible.

EXAMPLE 3

47g of Standard Method Agar Medium (Eiken) on the market were dissolved in 2l of water and bisected. One of them was dissolved 0.05g of TTC (Guaranteed reagent made by Wako Junyaku Co., Ltd.) therein and another was not added with TTC and used as a control.

Using these media, viable bacterial counts of soy bean curd was determined according to the same method as in Example 1. The result of counting was indicated similarly as in Example 1. The counting result of number of colony on each Petri dish was as shown in Table 6.

Table 6

| Kind of medium | Dilution ratio of sample | | | | | |
|---|---|---|---|---|---|---|
| | None | 10 | $10^2$ | $10^3$ | $10^4$ | $10^5$ |
| Medium of the present invention | ∞ | ∞ | 1444 | 142 | 19 | 1 |
| | ∞ | ∞ | 1430 | 157 | 16 | 3 |
| Control medium | +++ | +++ | +++ | +++ | +, 10 | 2 |
| | +++ | +++ | +++ | ++ | ++ | 5 |

(Note)
number of colonies is the number of colonies per 1ml of test suspension (Note) Number of colonies is the number of colonies per 1ml of test suspension As is evident from Table 6, in the present medium, above 1,400 each of the colonies could be counted so that viable bacterial counts in sample was determined as $15 \times 10^4$/g.

In contrast, in the control medium, exact viable bacterial counts could not be determined although it was determined below $30 \times 10^4$/g roughly according to the above described "Standard Methods of Examination of Dairy Products".

We claim:
1. A method for the quantitive determination of the viable bacteria count of food which is contaminated with spreading-colony forming bacteria by incubating said food in a liquified agar medium and subsequently counting the bacteria colonies, wherein the spreading of the bacteria colonies during incubation is inhibited by incubating said food in a liquified agar medium which contains from 0.005 to 0.1 grams of 2,3,5-triphenyl tetrazolium chloride per liter of said liquified agar medium.

2. A powdered agar medium for the quantitive determination fo the viable bacterial count of food which is contaiminated with spreading colony forming bacteria which comprises a nitrogen source, a carbon source, a phosphorous source, an ash source and an amount of 2,3,5-triphenyl tetrazolium chloride sufficient to yield a concentration of from 0.005 to 0.1 gram per liter when the agar medium is dissolved in water to inhibit colony spreading.

* * * * *